(12) United States Patent
Viola et al.

(10) Patent No.: US 8,592,464 B2
(45) Date of Patent: Nov. 26, 2013

(54) NITRIC OXIDE FUROXAN DERIVATIVE COMPOUNDS ENDOWED WITH ANTITUMORAL ACTIVITY

(75) Inventors: Antonella Viola, Rozzano (IT); Enzo Bronte, Rozzano (IT); Marco Crosetti, Rozzano (IT); Loretta Lazzarato, Rozzano (IT); Roberta Fruttero, Rozzano (IT); Alberto Gasco, Rozzano (IT)

(73) Assignees: Humanitas Mirasole S.p.A., Rossano (IT); Istituto Oncologico Veneto IRCCS, Pavoda (IT)

( * ) Notice: Subject to any disclaimer, the term of this patent is extended or adjusted under 35 U.S.C. 154(b) by 147 days.

(21) Appl. No.: 13/144,389

(22) PCT Filed: Jan. 15, 2010

(86) PCT No.: PCT/EP2010/050455
§ 371 (c)(1),
(2), (4) Date: Jul. 13, 2011

(87) PCT Pub. No.: WO2010/081877
PCT Pub. Date: Jul. 22, 2010

(65) Prior Publication Data
US 2012/0021007 A1  Jan. 26, 2012

(30) Foreign Application Priority Data
Jan. 15, 2009 (WO) ................ PCT/EP2009/000206

(51) Int. Cl.
*A61K 31/41* (2006.01)
*C07D 413/00* (2006.01)

(52) U.S. Cl.
USPC ............ 514/364; 514/340; 548/125; 548/126

(58) Field of Classification Search
USPC ......... 514/364, 340; 548/125, 126; 546/269.1
See application file for complete search history.

(56) References Cited

U.S. PATENT DOCUMENTS
7,799,782 B2 * 9/2010 Munson et al. ............ 514/234.5

FOREIGN PATENT DOCUMENTS
DE          44 20 523  A1   12/1995
WO    WO 2004/096793  A1   11/2004
WO       WO2007/060112   *  5/2007

OTHER PUBLICATIONS
Mijatovic et al. CAS: 148:553081, 2008.*

* cited by examiner

*Primary Examiner* — Rei-tsang Shiao
(74) *Attorney, Agent, or Firm* — Dickstein Shapiro LLP

(57) ABSTRACT

The present invention relates to nitric oxide furoxan derivative compounds which showed to be active in the treatment of tumors. In addition, they may be used as adjuvants in cancer immunotherapy.

5 Claims, 4 Drawing Sheets

NITRIC OXIDE FUROXAN DERIVATIVE COMPOUNDS ENDOWED WITH ANTITUMORAL ACTIVITY

FIELD OF THE INVENTION

The present invention pertains to the field of medicine; in particular, it concerns new furoxan derivative compounds able to inhibit some metabolic pathways involved in tumoral development.

BACKGROUND

Prostate cancer is the second leading cause of malignancy-related mortality in males in the Western world. While radical prostatectomy and local radiotherapy are largely successful for patients with localized cancer, available treatments for metastatic prostate carcinoma (PCa) have demonstrated weak curative efficacy. It is therefore necessary to find alternative therapeutic approaches to hormone-refractory metastatic prostate cancer. Immunotherapy may provide valid alternative therapy for patients with hormone-refractory metastatic PCa. The success of this approach depends on the ability of cytotoxic T cells to kill tumor cells. However, if the tumor environment exerts a suppressive action on antigen-specific tumor infiltrating lymphocytes (TIL), immunotherapy will achieve little, if any, successes. Thus, it is paramount to understand the cell biology of TIL and the modulation of TIL responses by the tumor environment.

The role of the prostate tumor environment in modulating T cell response have been analyzed with a study based on the use of collagen gel-matrix supported organ cultures of human PCa. The advantage of using this technique is that the microenvironment remains intact and all the factors that may affect TIL functions, such as cell-cell interaction, cell-matrix supported interaction and interstitial fluid, are preserved. This innovative approach to TIL biology allowed to obtain several important new findings.

In principle, TIL infiltrating PCa samples are mainly CD8+ T lymphocytes with an antigen-experienced, terminally differentiated phenotype (CD8+ CD45RA+ CD62L− CCR7−), positive for perforin and therefore able to kill the cancerous cells; however, they are in dormant state since they do not express activation markers such as CD25, CD69 and CD137. Moreover, different from normally responsive lymphocytes in tumor free prostates and peripheral blood, TIL are not activated locally by powerful signals acting either on TCR or downstream signaling pathways, indicating a tumor-restricted deficiency. In addition, evidence has been accumulating that arginase (ARG) and nitric oxide synthase (NOS) enzymes are over expressed in PCa as compared with hyperplasic prostate, with the intriguing observation that the tumor cells themselves rather than myeloid infiltrating cells could be the main source of the enzymes. The results indicate that the steady-state regulation of the dormant state is dependent on the enhanced intra-tumoral metabolism of the amino acid L-Arginine (L-Arg), since the simple addition of ARG and NOS specific inhibitors was sufficient to rouse these CTL, activate them and start a number of events leading to cytolitic granule polarization and killing of cognate targets. In addition, it has also been demonstrated the presence of high levels of nitrotyrosines in TILs, suggesting a local production of peroxynitrites, possibly due to ARG and NOS activities, since by inhibiting the activity of the enzymes a reduced tyrosine nitration was also achieved.

These results identify a mechanism by which human prostate cancer induces in situ immunosuppression. Thus, drug controlling the generation of reactive nitrogen species (RNS) might be useful to aid immunotherapeutic approaches for the treatment of cancer, by creating a favorable tumor environment for lymphocyte activation (Bronte et al., 2005).

Results from clinical trials have shown that the efficacy of different immunotherapeutic approaches is not adequate for an immediate and widespread transfer of this novel therapeutic approach to cancer patients. An important emerging concept is that the altered metabolism present in tumor microenvironment may have a profound impact on antitumor activity. Considering results mentioned above, it is clear that drugs controlling the generation of reactive nitrogen species (RNS) might enhance significantly the impact of immunotherapeutic approaches for the treatment of cancer. Accordingly, the present invention provides new furoxan compounds acting on the mechanisms of tumoral development.

SUMMARY OF THE INVENTION

Considering the strict relationship between ARG, NOS and cyclooxigenase enzymes, all over-expressed in prostate cancer cells as compared to normal prostate epithelium, the present invention concerns novel small molecules interfering with multiple and interconnected metabolic pathways. In contrast to conventional adjuvants, such as cytokines and activators of antigen presenting cells, which are characterized by broad action on the immune system, lack of selectivity and potentially important side effects, the molecules of the present invention potentiate the function of effector anti-tumor lymphocytes either spontaneously present, elicited in patients upon vaccination, or injected through an adoptive immunotherapy protocol.

OBJECT OF THE INVENTION

In first object, the present invention concerns N-oxides of 1,2,5-oxadiazole.

In a second embodiment, the present invention relates to the use of the compounds of the invention as a medicament and, as a preferred embodiment, to their use as medicaments for the therapy of pathologies characterized by the generation of reactive nitrogen species.

As a preferred embodiment, the compounds of the invention are used for the treatment of prostatic cancer.

As a third embodiment, the invention relates to a pharmaceutical preparation comprising the compounds of the invention.

In a further embodiment, the present invention relates to the use of the compounds of the invention as a vaccine against prostate cancer.

DETAILED DESCRIPTION OF THE INVENTION

Figure 1:
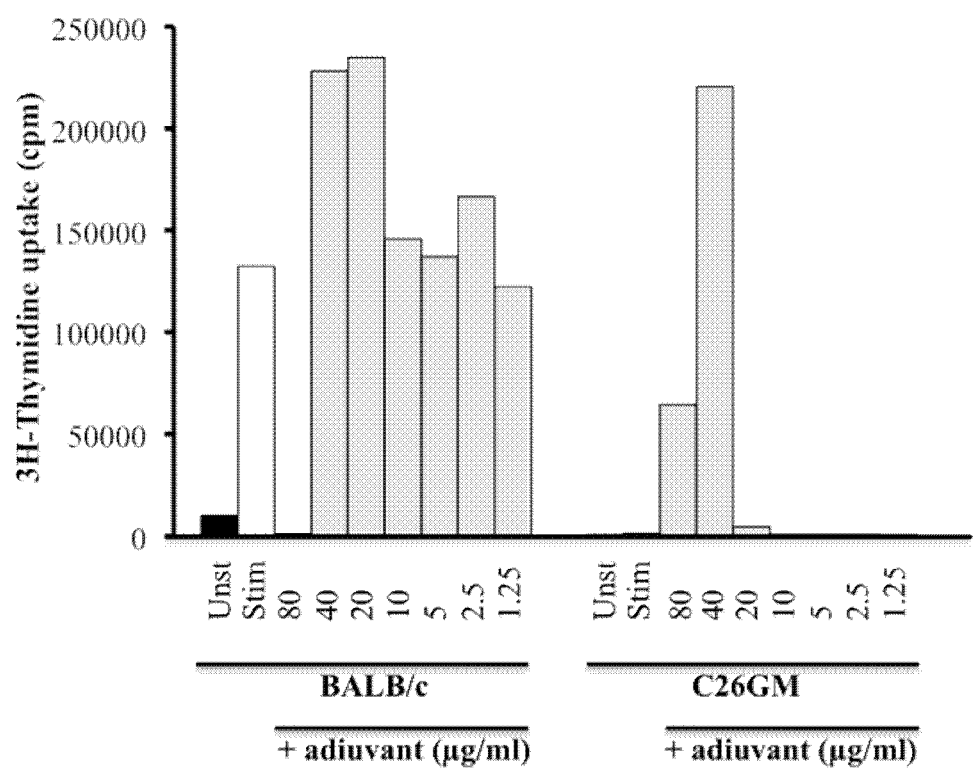
FIG. 1 shows the results of the proliferation assay.

In a first embodiment, the present invention relates to new furoxan compounds.

In particular, the compounds are those having general formula (I) below:

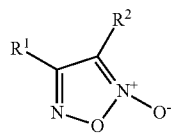

(I)

wherein

R¹ may be a C1-C8 straight or branched carbon chain or a C2-C8 linear or branched unsaturated carbon chain containing one or more double or triple bonds, optionally substituted with one or more acyloxy groups (—O—C(O)—R³), wherein R³ may be a C1-C8 straight or branched saturated or a C2-C8 straight or branched unsaturated carbo chain optionally substituted with an aryl group Ar, optionally substituted at any available positions with one or more hydroxyl (—OH), carboxy group (—COOH) or ester group (—COOR⁴), cyano (—CN), alkoxy (—O—R⁴), halogen, nitro (NO₂), amino (—NH₂), substituted amino (—NR⁴₂) wherein R⁴ is a C1-C8 straight or branched saturated carbon chain or a C2-C8 linear or branched unsaturated carbon chain containing one or more double or triple bonds, or R³ may be the aryl group Ar optionally substituted as above, or R¹ may be substituted with one or more ether (—O—R³) or tioether (—S—R³) groups, or R¹ may be an arylsulfonyl group (—SO₂Ar) wherein the aryl may be substituted at any available positions with one or more hydroxyl (—OH), carboxy group (—COOH) or ester group (—COOR⁴), cyano (—CN), alkoxy (—O—R⁴), halogen, trifluoromethyl (—CF₃), nitro (NO₂), amino (—NH₂), substituted amino (—NR⁴₂), or R¹ may be the Ar group or R¹ and R² together with the atoms they are linked to form a [1,2,5] oxadiazolo[3,4-e][2,1,3]benzoxadiazole 3,6-N-dioxide, and wherein R² may be a cyano group (—CN) or an amide group (—CONR⁵₂), wherein R⁵ may be each independently hydrogen or R⁴; and pharmaceutically acceptable salts thereof.

Preferably, within formula (I) above, R¹ is a methylene group (—CH₂—), substituted with an acyloxy group (—O—C(O)—R³), wherein R³ is methyl (—CH₃) or an aryl group Ar substituted at any available position with one or more hydroxyl (—OH), carboxy (—COOH), acyloxy (—COOR⁴) or ester group (—COOR⁴), being R⁴ as above disclosed, halogen, methyl (—CH₃), methoxy (—OCH₃), cyano (—CN) or R³ is —CH═CH— substituted with the aryl group Ar optionally substituted as above disclosed, or R¹ is substituted with a methoxy group (—OCH₃) or a salicylic acid residue, or R¹ is a phenylsulphonyl group (—SO₂Ph) and R² is a cyano (—CN) or an amido group (—CONH₂).

In a preferred embodiment, the compounds of the invention are those of formula (I) as above disclosed, wherein when R² is an amide group (—CONH₂) R¹ is not methyl (—CH₃) or R¹ is not an unsubstituted phenyl.

In a further preferred embodiment, the compounds of the invention are those of formula (I) above disclosed, provided that it is not one of the following:

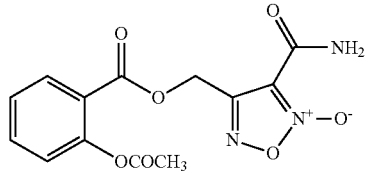

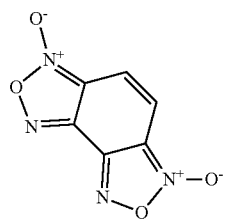
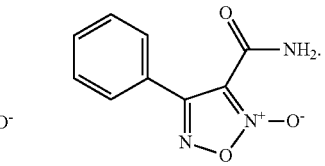

Within the scope of the present invention aryl group (Ar) includes C5-C14 aromatic monocyclic or bicyclic compounds, such as, for instance, benzene, naphthalene and their heteroaromatic corresponding compounds comprising one or more heteroatoms selected from the group comprising O, N, S, such as, for instance, furan, pyrrole, thiophene, imidazole, pyridine, benzothiophene, indole, quinoline, etc., wherein the preferred heterocycles are pyridine and quinoline.

When substituted, Ar group may be substituted at any available positions with one or more hydroxyl (—OH), carboxy (—COOH), ester (—COOR⁴), cyano (—CN), alkoxy (—O—R⁴), nitro (NO₂), amino (—NH₂) or substituted amino group (—NR⁴₂) or with an halogen, wherein R⁴ is a C1-C8 straight or branched saturated carbon chain or a C2-C8 linear or branched unsaturated carbon chain containing one or more double or triple bonds.

Halogen includes F, Cl, Br, I.

The preferred compounds of the invention, in particular, are those of the following formulae:

AT24

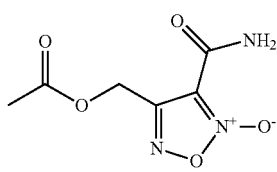

AT25

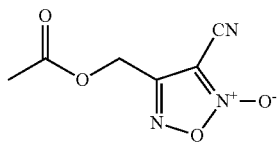

AT38

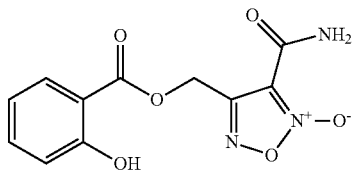

AT43

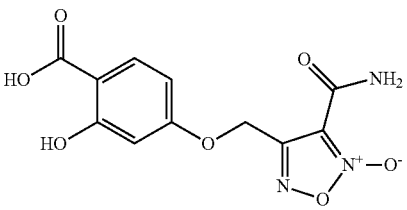

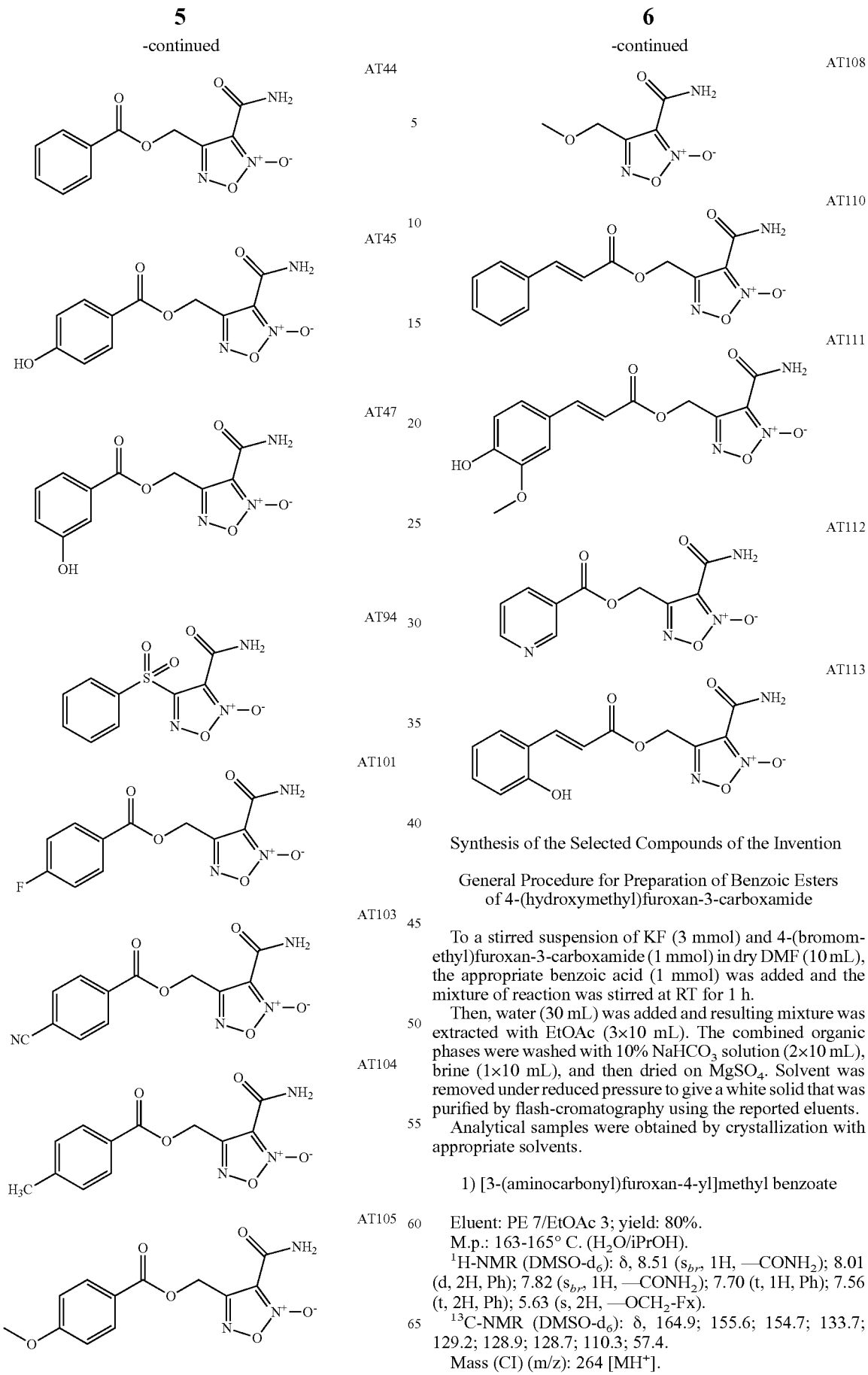

Synthesis of the Selected Compounds of the Invention

General Procedure for Preparation of Benzoic Esters of 4-(hydroxymethyl)furoxan-3-carboxamide To a stirred suspension of KF (3 mmol) and 4-(bromomethyl)furoxan-3-carboxamide (1 mmol) in dry DMF (10 mL), the appropriate benzoic acid (1 mmol) was added and the mixture of reaction was stirred at RT for 1 h.

Then, water (30 mL) was added and resulting mixture was extracted with EtOAc (3×10 mL). The combined organic phases were washed with 10% NaHCO$_3$ solution (2×10 mL), brine (1×10 mL), and then dried on MgSO$_4$. Solvent was removed under reduced pressure to give a white solid that was purified by flash-cromatography using the reported eluents.

Analytical samples were obtained by crystallization with appropriate solvents.

1) [3-(aminocarbonyl)furoxan-4-yl]methyl benzoate

Eluent: PE 7/EtOAc 3; yield: 80%.
M.p.: 163-165° C. (H$_2$O/iPrOH).
$^1$H-NMR (DMSO-d$_6$): δ, 8.51 (s$_{br}$, 1H, —CONH$_2$); 8.01 (d, 2H, Ph); 7.82 (s$_{br}$, 1H, —CONH$_2$); 7.70 (t, 1H, Ph); 7.56 (t, 2H, Ph); 5.63 (s, 2H, —OCH$_2$-Fx).
$^{13}$C-NMR (DMSO-d$_6$): δ, 164.9; 155.6; 154.7; 133.7; 129.2; 128.9; 128.7; 110.3; 57.4.
Mass (CI) (m/z): 264 [MH$^+$].

Anal. Calcd. for $C_{11}H_9N_3O_5$ C % 50.19, H % 3.45, N % 15.96. found C % 50.44, H % 3.58, N % 16.04.

2) [3-(aminocarbonyl)furoxan-4-yl]methyl salicylate

Eluent: $CH_2Cl_2$ 8/EtOAc 2; yield: 80%.

M.p.: 176-177° C. ($H_2O$/iPrOH).

$^1$H-NMR ($CDCl_3$): δ, 8.51 ($s_{br}$, 1H, —$CONH_2$); 7.86 (d, 1H, Ph); 7.59 ($s_{br}$, 1H, —$CONH_2$); 7.53 (t, 1H, Ph); 6.95 (m, 2H, Ph); 5.70 (s, 2H, —$OCH_2$-Fx).

$^{13}$C-NMR (DMSO-$d_6$): δ, 167.0; 159.8; 155.6; 154.0; 135.8; 130.2; 119.2; 117.6; 112.7; 110.4; 57.5.

Mass (CI) (m/z): 280 [$MH^+$].

Anal. Calcd. for $C_{11}H_9N_3O_6$ C % 47.32, H % 3.25, N % 15.05. found C % 47.36, H % 3.58, N % 14.97.

3) [3-(aminocarbonyl)furoxan-4-yl]methyl 3-hydroxybenzoate

Eluent: $CH_2Cl_2$ 8/EtOAc 2; yield: 82%.

M.p.: 203-204° C. ($H_2O$/iPrOH).

$^1$H-NMR (DMSO-$d_6$): δ, 9.91 (s, 1H, Ph-OH); 8.51 ($S_{br}$, 1H, —$CONH_2$); 7.83 ($s_{br}$, 1H, —$CONH_2$); 7.46-7.31 (m, 3H, Ph); 7.09-7.06 (m, 1H, Ph); 5.61 (s, 2H, —$COOH_2$-Fx).

$^{13}$C-NMR (DMSO-$d_6$): δ, 130.6; 165.7; 158.3; 156.4; 155.5; 130.7; 121.6; 120.9; 116.6; 111.2; 60.5.

Massa (CI) (m/z): 280 [$MH^+$].

Anal. Calcd. for $C_{11}H_9N_3O_6$ C % 47.32, H % 3.25, N % 15.05. found C % 46.97, H % 3.18, Na 15.45.

4) [3-(aminocarbonyl)furoxan-4-yl]methyl 4-hydroxybenzoate

Eluent: $CH_2Cl_2$ 8/$CH_3OH$ 2; yield: 50%.

M.p.: 241-242° C. ($H_2O$/iPrOH).

$^1$H-NMR (DMSO-$d_6$): δ, 10.44 (s, 1H, Ph-OH); 8.49 ($S_{br}$, 1H, —$CONH_2$); 7.85 (d, 2H, Ph); 7.82 ($s_{br}$, 1H, —$CONH_2$); 6.87 (d, 2H, Ph); 5.55 (s, 2H, —$OCH_2$-Fx).

$^{13}$C-NMR (DMSO-$d_6$): δ, 164.7; 162.4; 155.6; 154.9; 131.7; 119.2; 115.4; 110.3; 57.0.

Mass (CI) (m/z): 280 [$MH^+$].

Anal. Calcd. for $C_{11}H_9N_3O_6$ C % 47.32, H % 3.25, N % 15.05. found C % 47.29, H % 3.25, N % 15.17.

5) [3-(aminocarbonyl)furoxan-4-yl]methyl 4-fluorobenzoate

Eluent: $CH_2Cl_2$ 8/EtOAc 2; yield: 90%.

M.p.: 163-164° C. ($H_2O$/iPrOH).

$^1$H-NMR (DMSO-$d_6$): δ, 8.52 ($S_{br}$, 1H, —$CONH_2$); 8.08 (m, 2H, Ph); 7.83 ($S_{br}$, 1H, —$CONH_2$); 7.37 (t, 2H, Ph); 5.62 (s, 2H, —$OCH_2$-Fx).

$^{13}$C-NMR (DMSO-$d_6$): δ, 165.3 (d, $J^1_{CF}$=270 Hz); 164.0; 155.6; 154.6; 132.3 (d, $J^3_{CF}$=9.75 Hz); 125.3; 116.0 (d, $J^2_{CF}$=22.2 Hz); 110.4; 57.6.

Mass (CI) (m/z): 282 [$MH^+$].

Anal. Calcd. for $C_{11}H_8N_3O_5F$ C % 46.98, H % 2.87, N % 14.94. found C % 47.10, H % 2.86, Na 15.00.

6) [3-(aminocarbonyl)furoxan-4-yl]methyl 4-nitrobenzoate

Eluent: $CH_2Cl_2$ 9/EtOAc 1; yield; 86%.

M.p.: 172-173° C. ($H_2O$/iPrOH).

$^1$H-NMR (DMSO-$d_6$): δ, 8.53 ($S_{br}$, 1H, —$CONH_2$); 8.28 (d, 2H, Ph); 8.25 (d, 2H, Ph); 7.85 ($s_{br}$, 1H, —$CONH_2$); 5.76 (s, 2H, —$COOH_2$-Fx).

$^{13}$C-NMR (DMSO-$d_6$): δ, 163.5; 155.4; 154.3; 150.4; 134.1; 130.8; 123.9; 110.4; 58.1.

Mass (CI) (m/z): 309 [$MH^+$]

Anal. Calcd. for $C_{11}H_8N_4O_7$ C % 42.87, H % 2.62, N % 18.18. found 0% 42.85, H % 2.67, N % 18.05.

7) [3-(aminocarbonyl)furoxan-4-yl]methyl 4-cyanobenzoate

Eluent: $CH_2Cl_2$ 9/EtOAc 1; yield: 87%.

M.p.: 190-191° C. ($CHCl_3$/n-Hex).

$^1$H-NMR (DMSO-$d_6$): δ, 8.51 ($s_{br}$, 1H, —$CONH_2$); 8.15 (d, 2H, Ph); 8.14 (d, 2H, Ph); 7.82 ($s_{br}$, 1H, —$CONH_2$); 5.66 (s, 2H, —$OCH_2$-Fx).

$^{13}$C-NMR (DMSO-$d_6$): δ, 163.7; 155.5; 154.4; 132.9; 132.6; 129.9; 117.9; 115.8; 110.4; 57.9.

Mass (CI) (m/z): 289 [$MH^+$].

Anal. Calcd. for $C_{12}H_8N_4O_5$ 0% 50.01, H % 2.79, N % 19.44. found C % 50.13, H % 2.84, N % 19.48.

8) [3-(aminocarbonyl)furoxan-4-yl]methyl 4-methylbenzoate

Eluent: $CH_2Cl_2$ 9.5/EtOAc 0.5; yield: 68%.

M.p.: 149-150° C. ($H_2O$/iPrOH).

$^1$H-NMR (DMSO-$d_6$): δ, 8.51 ($S_{br}$, 1H, —$CONH_2$); 7.90 (d, 2H, Ph); 7.84 ($S_{br}$, 1H, —$CONH_2$); 7.37 (d, 2H, Ph); 5.61 (s, 2H, —$OCH_2$-Fx); 2.41 (s, 3H, Ph-$CH_3$).

$^{13}$C-NMR (DMSO-$d_6$): δ, 164.8; 155.5; 154.7; 144.2; 129.4; 129.3; 125.9; 110.3; 96.9; 57.3.

Mass (CI) (m/z): 278 [$MH^+$].

Anal. Calcd. for $C_{12}H_{11}N_3O_5$ C % 51.98, H % 3.99, N % 15.16. found 0% 52.10, H % 3.99, N % 15.14.

9) [3-(aminocarbonyl)furoxan-4-yl]methyl 4-methoxybenzoate

Eluent: $CH_2Cl_2$ 9/EtOAc 1; yield: 95%.

M.p.: 175-176° C. ($H_2O$/iPrOH).

$^1$H-NMR (DMSO-$d_6$): δ, 8.50 ($S_{br}$, 1H, —$CONH_2$); 7.94 (d, 2H, Ph); 7.83 ($S_{br}$, 1H, —$CONH_2$); 7.06 (d, 2H, Ph); 5.83 (s, 2H, —$OCH_2$-Fx); 3.85 (s, 3H, —$OCH_3$).

$^{13}$C-NMR (DMSO-$d_6$): δ, 164.5; 163.5; 155.6; 154.8; 131.5; 120.8; 114.1; 110.3; 57.2; 55.5.

Mass (CI) (m/z): 294 [$MH^+$].

Anal. Calcd. for $C_{12}H_{11}N_3O_6$ C % 49.15, H % 3.78, N % 14.33. found C % 49.27, H % 3.79, N % 14.33.

10) [3-(aminocarbonyl)furoxan-4-yl]methyl 4-aminobenzoate

Eluent: $CH_2Cl_2$ 9/EtOAc 1; yield: 89%.

M.p.: 206-208° C. ($H_2O$/iPrOH).

$^1$H-NMR (DMSO-$d_6$): δ, 8.50 ($s_{br}$, 1H, —$CONH_2$); 7.83 ($s_{br}$, 1H, —$CONH_2$); 7.69 (d, 2H, Ph); 7.59 (d, 2H, Ph); 6.09 (s, 2H, —$NH_2$); 5.52 (s, 2H, —$OCH_2$-Fx).

$^{13}$C-NMR (DMSO-$d_6$): δ, 164.9; 155.6; 155.2; 153.9; 131.4; 114.4; 112.6; 110.3; 56.6.

Mass (CI) (m/z): 279 [$MH^+$].

Anal. Calcd. for $C_{11}H_{10}N_4O_5$ 0% 47.48, H % 3.62, N % 20.14. found C % 47.31, H % 3.60, N % 20.20.

11) [3-(aminocarbonyl)furoxan-4-yl]methyl 4-chlorobenzoate

Eluent: $CH_2Cl_2$ 9/EtOAc 1; yield: 98%.

M.p.: 171-172° C. (n-Hex/iPrOH).

$^1$H-NMR (DMSO-d$_6$): δ, 8.51 (s$_{br}$, 1H, —CONH$_2$); 8.02 (d, 2H, Ph); 7.83 (S$_{br}$, 1H, —CONH$_2$); 7.65 (d, 2H, Ph); 5.63 (s, 2H, —OCH$_2$-Fx).

$^{13}$C-NMR (DMSO-d$_6$): δ, 164.1; 155.5; 154.5; 138.7; 130.8; 129.0; 127.6; 110.4; 57.7.

Mass (CI) (m/z): 298 [MH$^+$].

Anal. Calcd. for C$_{11}$H$_8$N$_3$O$_5$Cl C % 44.38, H % 2.71, N % 14.12. found C % 44.32, H % 2.75, N % 14.13.

It is submitted that the person skilled in the art will be able to prepare other compounds falling within the scope of the present invention without undue burden.

Materials and Methods

Cell Lines and Mice

CT26 (H-2d), a BALB/c carcinogen-induced colon carcinoma; MBL-2 (H-2b), a Moloney virus-induced lymphoma; C26-GM, a cell line derived from the C26 colon carcinoma (H-2d) genetically modified to release granulocyte-macrophage colony-stimulating factor (GM-CSF).

Cells were grown in DMEM (Invitrogen) or in RPMI medium 1640 (Euroclone) supplemented with 2 mM L-glutamine, 10 mM Hepes (DMEM) or 1 mM sodium pyruvate (RPMI 1640), 20 mM 2-mercaptoethanol, 150 units/ml streptomycin and 200 units/ml penicillin, 10% heat-inactivated FBS (Invitrogen or BioWhittaker).

BALB/c (H-2$^d$) and C57BL/6 (H-2$^d$) mice (8 weeks old) were purchased from Harlan.

BALB/c mice were inoculated s.c. in the inguinal fold with 0.5×10$^6$ C26GM cells. Mice were killed after 9 days and splenocytes were used for in vitro assay.

For in vivo experiments, BALB/c mice were inoculated s.c. on the left flank with 0.5×10$^6$ C26GM cells.

Proliferation Assay

BALB/c splenocytes from control animals and from colon-carcinoma26 (C26GM) tumor bearing-mice were plated at 6×10$^5$ cells/well and stimulated with 3 μg/ml anti-CD3 (2C11, ATCC) and 2 μg/ml anti-CD28 (clone 37.5, ATCC) either with or without scalar dilutions of each furoxan derivate as adjuvant. After 2 days of incubation, 1 μCi/well (1 Ci=37 GBq) of $^3$H-TdR (PerkinElmer) was added to the cultures for 18 h, and $^3$H-TdR incorporation was measured by scintillation counting.

Chromium Release Assay

Two different cell cultures were set up to evaluate the CTL response. First, BALB/c splenocytes (6×10$^5$ cells/well) were stimulated with (6×10$^5$ cells/well) γ-irradiated C57BL/6 splenocytes in 96-well, flat-bottom plates (BD Falcon), either with or without furoxan derivates at scalar dilutions. To obtain immunosuppression, CD11b$^+$ cells sorted from the spleens of tumor-bearing mice were added at a final concentration of 3% to a mixed leucocytes culture. Second, immunosuppressed splenocytes (6×10$^5$ cells/well) derived from tumor-bearing mice were stimulated with γ-irradiated C57BL/6 splenocytes (6×10$^5$ cells/well) in 96-well, flat-bottom plates either with or without furoxan derivates at scalar dilutions. The percentage of CD11b$^+$ cells present in the spleen of these mice varied from 20 to 40%.

In both experimental conditions, after 5 days of incubation, cultures were tested for ability to kill 2×10$^3$ allogenic (MBL-2) or singenic (CT26) target cells in a 5-h $^{51}$Cr-release assay.

The percentage of specific lysis was calculated from triplicate samples as follows: (experimental cpm-spontaneous cpm)/(maximal cpm-spontaneous cpm)×100, whereas litic unit 30 (LU30) represent the number of CTL cells required to kill 30% of target cells.

Immunohistochemistry

The tumors were fixed in PLP fixative (Paraformaldehyde/Lysine/Periodate), cryoprotected in 30% sucrose and frozen in OCT. The samples were cut with a cryostat (6 mm) and after air drying, the sections were fixed with acetone for 3 min. Subsequently, the slides were rehydrated with PBS and endogenous peroxidase activity and the aspecific sites were blocked. The tissue sections were incubated with the primary antibodies anti-Nitrotyrosine (1:200, Calbiochem) or anti-CD3 (1:50, Dako) for 2 h at r.t. After washes with PBS, the samples were incubated with goat-anti-rabbit-peroxidase (Dako) for 1 h at r.t. Immunoreactivity was visualized with 3,3-diaminobenzidine (DAB). Sections were counterstained with hematoxylin and mounted in Eukitt.

Adoptive Cell Therapy

Figure 4:
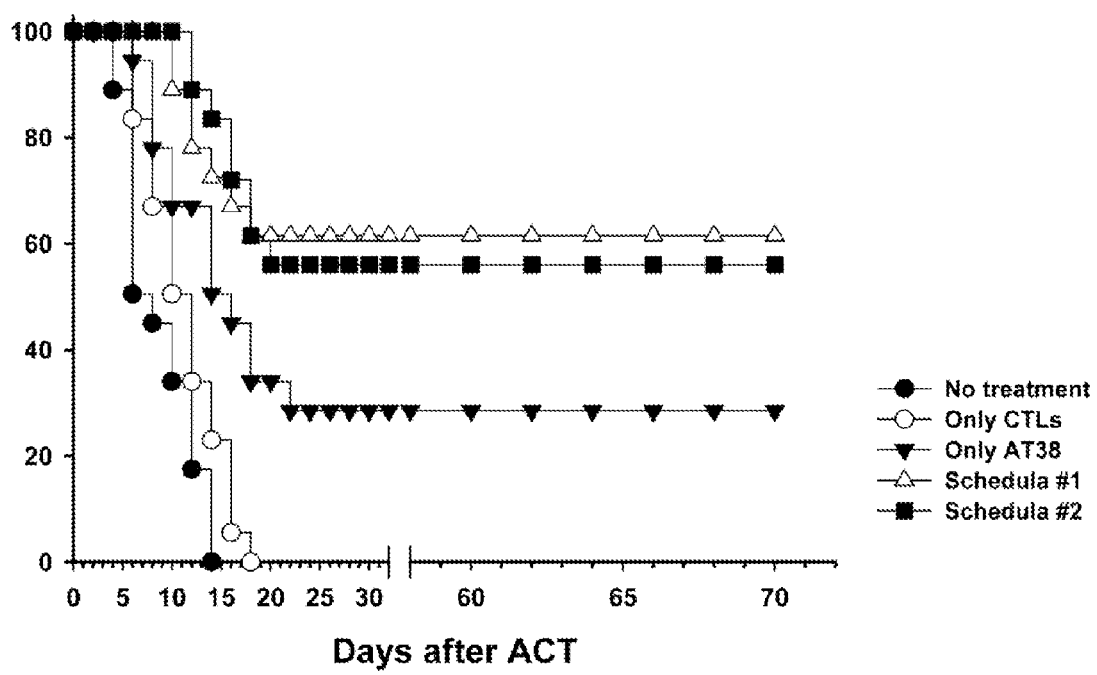
FIG. 4 shows the results of the in vivo experiments on compound AT38.

Adoptive cell therapy (ACT) was performed after inoculation of C57BL/6 mice with 10$^5$ EG-7 tumor cells subcutaneously on day 0. Tumor was allowed to grow and, at day 6, drug treatment was started. Mice were divided in 5 groups: tumor growth control (receiving only carboxymethylcellulose); adoptive transfer of tumor-antigen specific CTLs; AT38 alone; schedule 1 (mice were treated continuously after day 6 till sacrifice) together with adoptive transfer; schedule 2 (drug was suspended the day after cells transfer) and adoptive cell transfer. Treated mice received AT38 at 30 mg/kg/die divided in 2 doses of 15 mg/kg every 12 hours. On day 10, 5×10$^6$ tumor antigen-specific CTLs were injected i.v. and mice were then treated i.p. with 30,000 IU of recombinant IL-2 twice a day for 3 consecutive days. On day 14 mice were sacrificed and tumors were taken for immunohistochemical analysis. Other mice were followed for survival as shown in FIG. 4.

Results

TABLE 1

| COMPOUNDS | in vitro lympho-proliferation Range of concentration to rescue T cell proliferation (μM) C26GM spleen | in vitro cytotoxicity assay Range of concentration to rescue cytolytic activity (μM) | |
|---|---|---|---|
| | | B6+C26GM | B6+Balb+ 3% CD11b+ |
| AT24 | 100-12.5 | INEFFECTIVE | INEFFECTIVE |
| AT25 | 25-6.25 | INEFFECTIVE | not yet tested |
| AT27 | 63-13 | 25 | 63-32 |
| AT38 | 72-18 | 25 | 72-34 |
| AT43 | 68 | INEFFECTIVE | 68-17 |
| AT44 | 76-38 | INEFFECTIVE | 76 |
| AT45 | 72-9 | 100 | 72 |
| AT47 | 72-18 | 50 | 72-18 |
| AT84 | 100 | 50-25 | 50-25 |
| AT88 | 19-6.25 | 1.25 μg/ml | 6.25-3.1 |
| AT94 | 19-9 | INEFFECTIVE | 10-5 |
| AT101 | 285-142 | 100-50 | not yet tested |
| AT103 | 140 | 100-50 | not yet tested |
| AT104 | 140 | 100-50 | not yet tested |
| AT105 | 273-68 | 100-50 | not yet tested |
| AT108 | 1.8 × 10$^3$ | Not yet tested | not yet tested |
| AT110 | 200-100 | 100 | not yet tested |
| AT111 | 100 | 100-50 | not yet tested |
| AT112 | 200 | 200 | not yet tested |
| AT113 | 50 | 100 | not yet tested |

Table 1 above reports a partial list of compounds that have been screened. The second column from left reports the minimal effective concentration of each furoxan adjuvant required to restore the T cell proliferation in immunosuppressive condition. Twenty out of 95 adjuvants restored T lymphocytes responsiveness, which was inhibited by the presence of myeloid suppressor cells.

Adjuvants, which demonstrate to be ineffective in a proliferation assay were discarded, while the others were tested in a cytotoxicity assay to evaluate their efficacy in restoring T cell cytolytic activity against allogenic target cells using two different immunosuppressive conditions (third and fourth column from left).

Nine out of twenty compounds completely restored the cytolytic function of CD8+ T cells in the alloreactive cultures containing 3% of immunosuppressive CD11b+ cells, one is ineffective (fourth column).

Under strong immunosuppressive conditions (third column) 14 of 20 compounds restored the alloreactivity of CD8+ T cells, whereas 5 of 20 were ineffective.

FIG. 1 shows the results of one representative assay among those performed (results for other 19 compounds were similar). In particular, it can be seen that adjuvant used in this assay restored T lymphocytes responsiveness inhibited by the presence of myeloid suppressor cells. No toxic effects were observed on control cell coltures by the furoxan derivate since scalar dilution of each compound does not affect lymphocyte proliferation of control BALB/c cell coltures (left panel), whereas restored the proliferation under immunosuppressive conditions (right panel).

Figure 2:
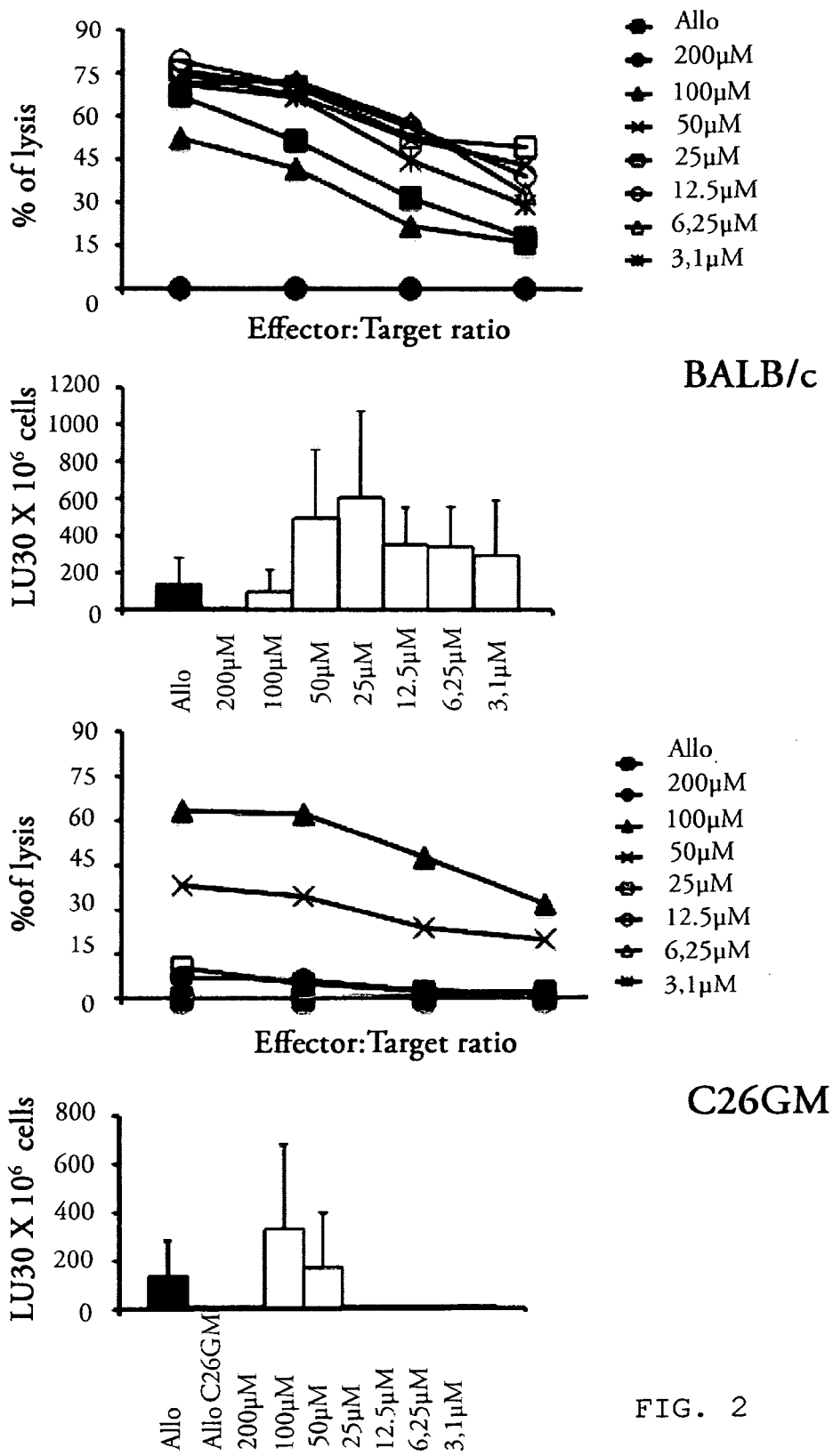
FIG. 2 shows the results of the chromium assay.

FIG. 2 depicts the results of a representative chromium release assay. A single dose of each compound was added at time 0 to the alloantigen-stimulated T cell coltures. In the upper panel, scalar dilutions of the furoxan derivate do not to affect the cytolitic activity of BALB/c control cell coltures except at the higher dose (200 μM). Under immunosuppressive conditions, 100 μM and 50 μM of furoxan derivate are able to restore the cytolytic functions of CD8+ T cell as shown by $LU_{30}/10^6$ cells that is comparable to the control. No effect was seen at lower concentrations. These data are representative of one compound, the other 19 showing similar results.

We also evaluated the solubility in physiological vehicles and the stability at pH 2 for 24 h in order to understand if we could perform an oral-administration of the adjuvants.

Figure 3:
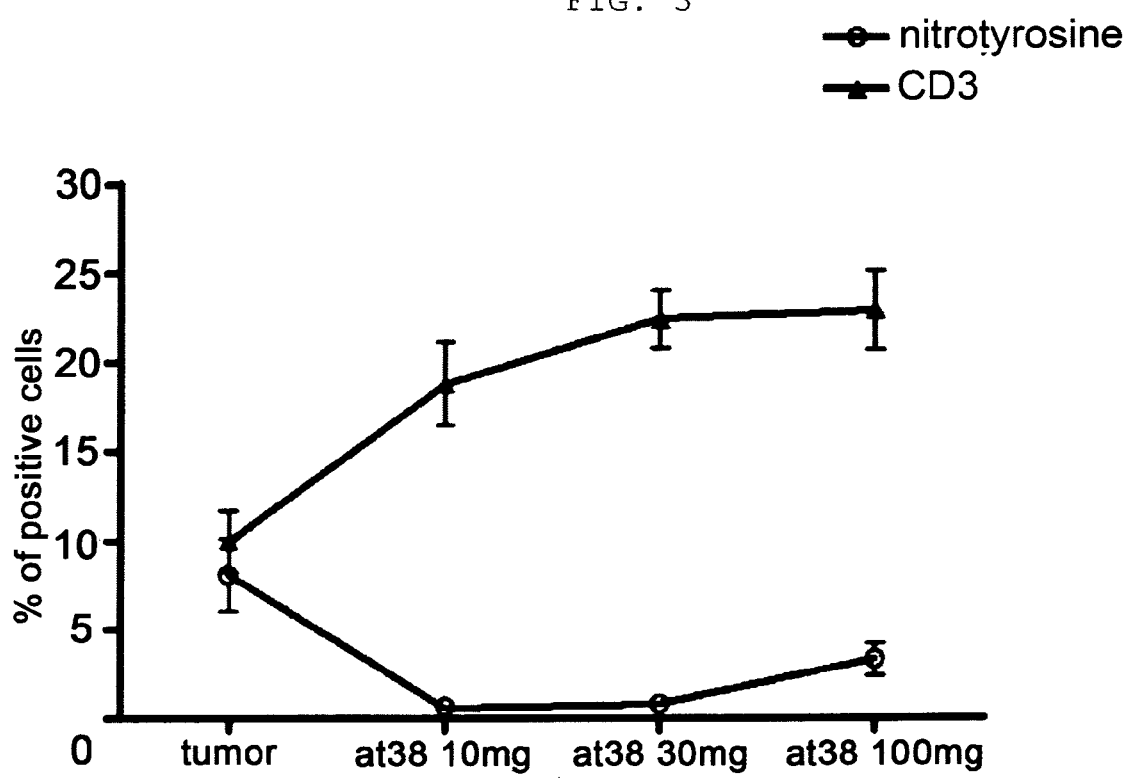
FIG. 3 shows a graph of the immunohistochemal analysis.

Based on the findings, it was investigated whether the compound AT38 could be useful in antitumor immunity elicited by cancer vaccination in tumor-bearing mice. The animals were injected subcutaneously with coloncarcinoma26 at day 0. The animals were treated for nine days with 3 different doses of AT38 (10, 30 and 100 mg/kg/day) orally administered starting from day 0 (see FIG. 3). At day 10 the animals were euthanized and tumors removed for immunohistochemistry analysis. Compared to untreated controls, animals that have received AT38 for nine days showed an enhancement of CD3+ T tumor infiltrating lymphocytes and a strong reduction of nitrotyrosine staining.

According to the above, it is a second object of the invention the use of the compounds of the invention as a medicament.

In a preferred embodiment, they are used for the treatment of pathologies characterized by the generation of RNS (reactive nitrogen species), such as, for instance, neoplasia, inflammatory diseases or chronicle infections.

In a still preferred embodiment, the compounds of the invention may be used for the treatment of prostate cancer.

In particular, the compounds which may be used are those of general formula (I) above and, according to a preferred embodiment, they are the compounds having the following formulae:

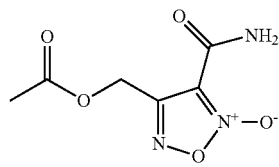
AT24

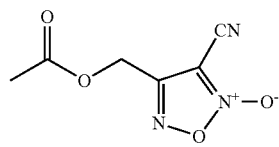
AT25

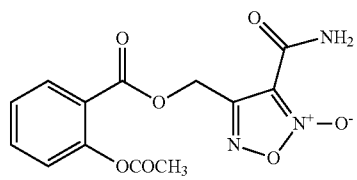
AT27

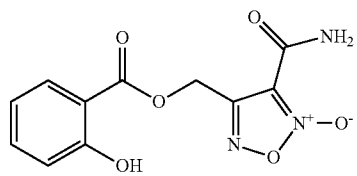
AT38

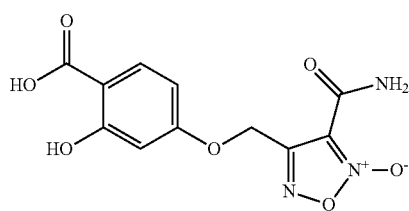
AT43

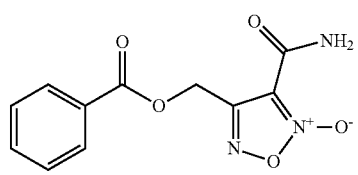
AT44

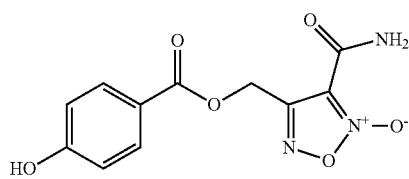
AT45

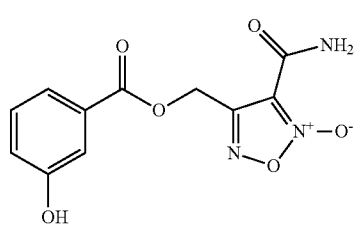
AT47

-continued

AT84 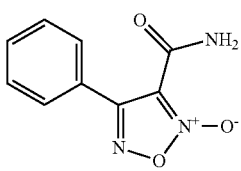

AT88 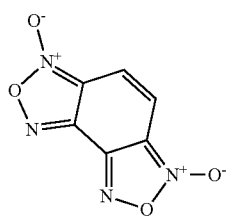

AT94 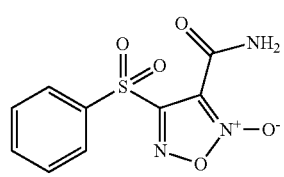

AT101 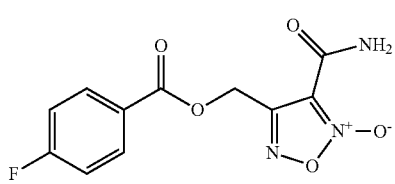

AT103 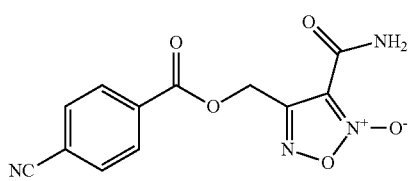

AT104 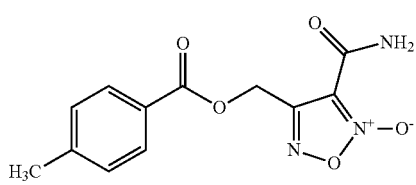

AT105 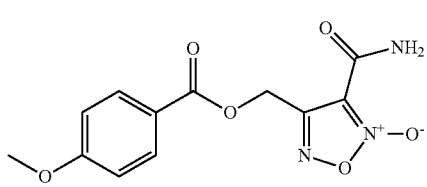

AT108 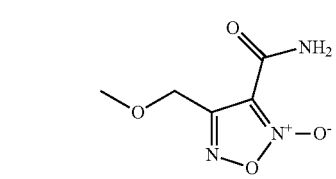

-continued

AT110 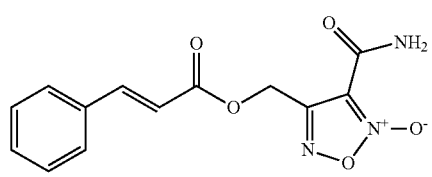

AT111 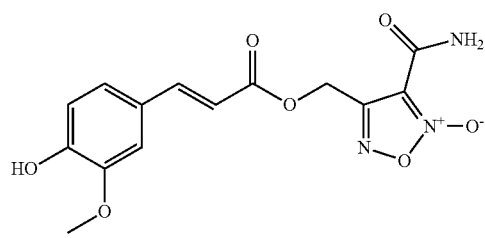

AT112 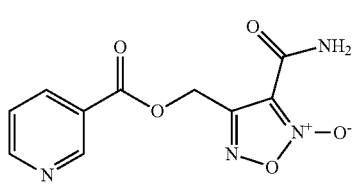

AT113 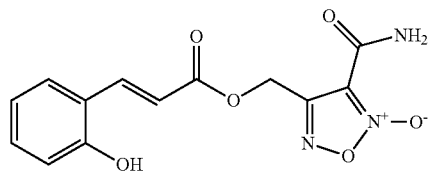

As per the above, it is a third object of the invention, the use of the disclosed compounds as adjuvant in the immunotherapeutic protocols against the above mentioned pathologies and, in particular, against malignant cancer.

For the purposes of the present invention, the disclosed compounds may be formulated, together with excipients and additives selected in the group comprising diluent, solvents, bulking agents, fillers, reological modifier, stabilizers, binders, lubricants, disintegrant, preservatives, pH adjusting agents, buffers, antioxidant, chelating agents, plasticizer, polymers, emulsifiers, edulcorants, flavoring agents; alone or in combination thereof, to give a pharmaceutical preparation as per the third embodiment of the invention. In particular, "pharmaceutically acceptable salt" is intended to include any salts suitable to be administered to human or animal and having suitable technological properties, such as, for instance, sodium, potassium, ammonium, zinc salt or any salts with amino acids (see, for a general reference, Remington's Pharmaceutical Sciences Handbook, Mack Pub. Co., N.Y., USA 17$^{th}$ edition, 1985).

The invention claimed is:
1. A compound of formula

AT38 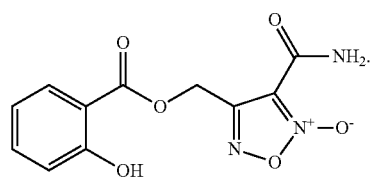

2. A method for the treatment of pathologies characterized by the generation of reactive nitrogen species comprising the administration of the compound of claim 1.

3. The method for the treatment of pathologies characterized by the generation of reactive nitrogen species according to claim 2, wherein said pathologies comprise neoplasia, inflammatory diseases or chronicle infections.

4. The method for the treatment of pathologies characterized by the generation of reactive nitrogen species according to claim 2, wherein said pathology is prostate cancer.

5. A method for potentiating the function of antitumor lymphocytes comprising the administration of the compound

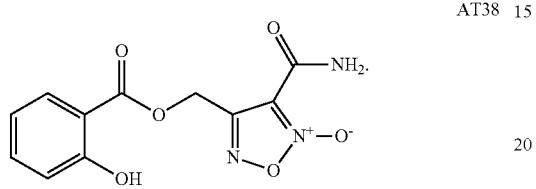

AT38

* * * * *